Figure 1:
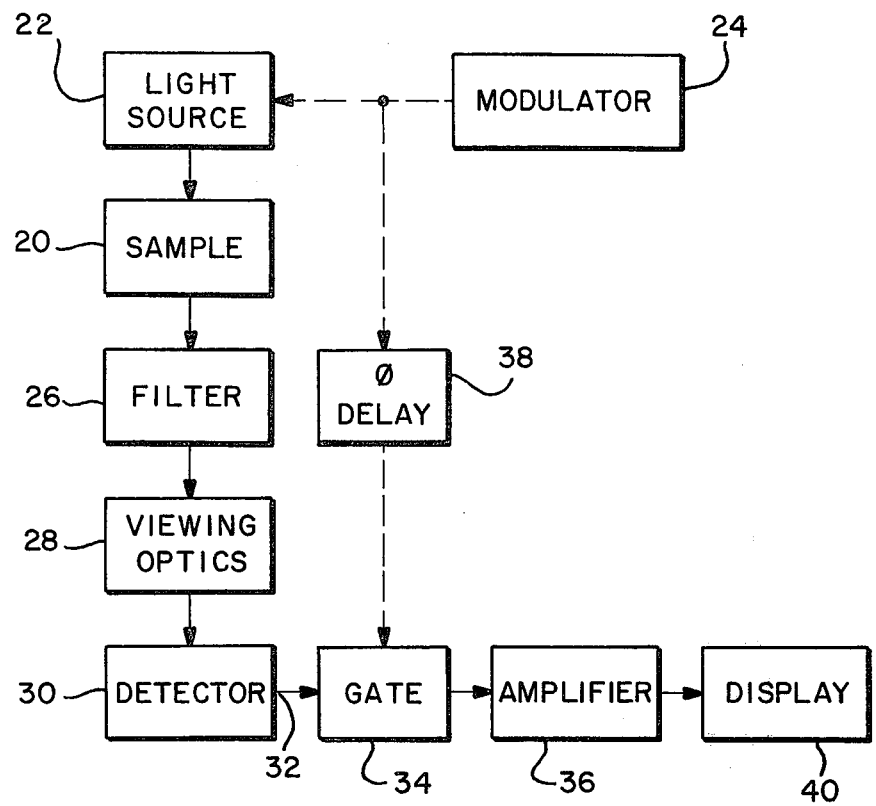

United States Patent [19]

Mueller

[11] 4,006,360
[45] Feb. 1, 1977

[54] METHOD OF DISCRIMINATING BETWEEN DYED PARTICLES AND BACKGROUND FLUORESCENCE OF THE DYE

[75] Inventor: William A. Mueller, Dedham, Mass.

[73] Assignee: Block Engineering, Inc., Cambridge, Mass.

[22] Filed: Jan. 2, 1976

[21] Appl. No.: 646,324

Related U.S. Application Data

[63] Continuation of Ser. No. 499,132, Aug. 21, 1974, abandoned.

[52] U.S. Cl. ............................ 250/461 B; 250/373
[51] Int. Cl.² ....................................... G01M 21/38
[58] Field of Search .............. 250/461, 461 B, 372, 250/373

[56] References Cited

UNITED STATES PATENTS 3,886,363  5/1975  Ohnishi et al. ................. 250/461 B
3,918,812  11/1975  Holm ............................ 250/461 B

OTHER PUBLICATIONS

"Instrument To Measure Fluorescent Lifetime —" by Bennett, Review of Scientific Instruments, vol. 31, No. 12, Dec. 1960, pp. 1275–1279.

"Instrument To Measure Fluorescent Lifetimes —" by Brody, Review of Scientific Inst., vol. 28, No. 12, Dec. 1957, pp. 1021–1026.

"N(3-Pyrene) maleimide: A Long Lifetime Fluro. Sulfhydryl Reagent" by Weltman et al., Journal of Biological Chemistry, May 1973, pp. 3173, 3176.

"Lifetime–Separated Spectroscopy: —" by Pruett et al., Journal of Chemistry & Physics, vol. 62, No. 6, Mar. 15, 1975, pp. 2050–2056.

"Sensitized Fluorescence Measurements —" by Pace et al., Journal of Physics E: Scientific Instrument, 1974, vol. 7.

Fluoresence Assay in Biology & Medicine, vol. II, by Sidney Udenfriend, Academic Press, 1969, pp. 82, 83, 162, 163.

*Primary Examiner*—Harold A. Dixon
*Attorney, Agent, or Firm*—Schiller & Pandiscio

[57] ABSTRACT

A system for discriminating between the fluorescent emission from dye molecules bound to biological particles and the background emission from free molecules of the dye in the solution suspending the particles, where the quantum efficiency of the bound dye molecules because of their bound state, differs from the quantum efficiency of the unbound dye so that the emission from the bound dye exhibits a longer statistical decay lifetime. The system involves irradiating the particles in the solution with a mode locked laser, and measuring fluorescent intensity in delayed synchronism with the mode locking frequency.

8 Claims, 2 Drawing Figures

METHOD OF DISCRIMINATING BETWEEN DYED PARTICLES AND BACKGROUND FLUORESCENCE OF THE DYE

This application is a continuation of U.S. application Ser. No. 499,132 filed Aug. 21, 1974 and now abandoned.

This application relates to the detection of minute particles and more particularly to the detection of minute biological materials by fluorescent emission.

A common method of detecting minute biological specimens such as cells and the like is to differentially dye the cells with stains which, when bound to the specimen, will emit a characteristic fluorescence upon appropriate excitation. When a sample is stained with a comparatively dilute solution of dye, the concentration of the stain bound to the particles is often considerably higher than the average concentration of stain in the dye solution. The higher level of emission from the local concentrations of stain caused by binding will ordinarily permit one to discriminate the dyed specimens from background emission from the fluorescing dye in the staining solution.

In order to enhance the discrimination between the emission from the bound stain and the background emission, one can of course wash the specimen if the specimens can be physically separated from the dye solution. A number of fluorescent dyes have not been considered useful for staining biological samples in situations where the dye could not be washed out because the specimens could not be detected against the intense background fluorescence provided. Because washing is not always feasible the art has turned to fluorochrome dyes, i.e. dyes which will fluoresce weakly (or not at all) under excitation unless they are bound to the biological substrate.

Where however, the specimen size is very small (e.g. nucleic acids and the like) the problem of discrimination becomes severe. For example, the minimum volume of sample that can be viewed is diffraction limited. Hence, specimens much smaller than that minimum volume have poorer signal-to-noise ratios with respect to background.

Other factors, not necessarily related to specimen size, may also make the signal-to-background discrimination for specimens difficult. For example, the partition ratio (i.e. the ratio of concentration of dye in the specimens to the concentration of dye in the background) may be low. Also, the increase in quantum efficiency of fluorochrome dyes on becoming bound to a biological substrate may not be large.

A principal object of the present invention is therefore to provide a system for discriminating fluorescing dyed specimens from a background of fluorescence due to dye molecules dispersed in a liquid medium. To this end, the system of the present invention comprises a source of radiation which can stimulate fluorescent emission from dye molecules bound to specimens and from the free dye molecules dispersed in the staining medium. Means are provided for modulating the intensity of radiation from the source. Preferably the latter is a switching system so that the rise and decay times of the stimulating radiation are very short. Lastly, in the system of the present invention, following exposure of dyed specimens and background dye to stimulating radiation, the amplitude of fluorescent emission is determined starting at a predetermined time interval after the stimulating emission has been modulated "off", and the fluorescent emission is thereafter monitored for a predetermined period during which the stimulating radiation remains modulated "off".

Other objects of the invention will in part be obvious and will in part appear hereinafter. The invention accordingly comprises the apparatus possessing the construction, combination of elements, and arrangement of parts, and the method comprising the several steps and order thereof, all of which are exemplified in the following detailed disclosure, and the scope of the application of which will be indicated in the claims.

Figure 2:
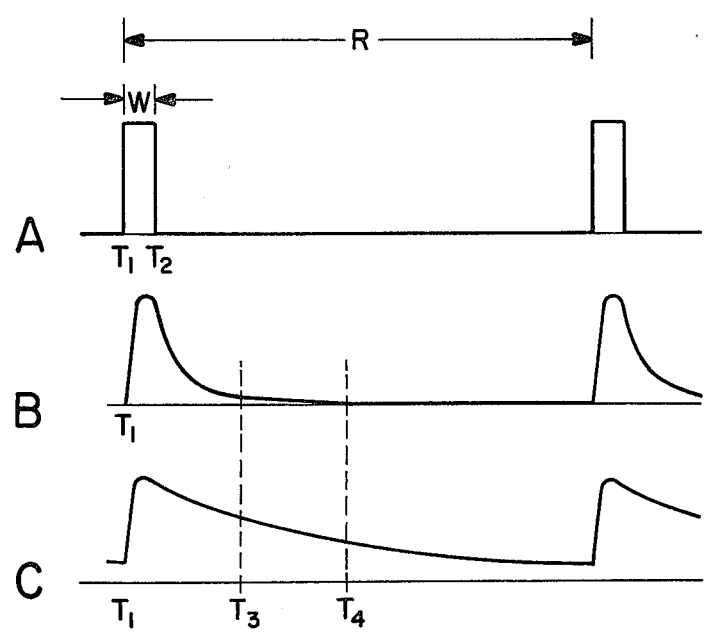

For a fuller understanding of the nature and objects of the present invention, reference should be had to the following detailed description taken in connection with the accompanying drawings wherein:

FIG. 1 is a block diagram showing an exemplary system embodying the principles of the present invention; and FIG. 2 is a timing diagram showing the operation of the system of FIG. 1.

In many instances, the quantum efficiency ($Q_E$) of a fluorescent dye (i.e. the ratio of emitted quanta to absorbed quanta) differs depending upon whether the dye is bound or not bound to a substrate. This is particularly true with respect to fluorochrome dyes. If the $Q_E$ of two identical dye molecules thus differs, the lifetimes of their excited states are different. The present invention employs this difference in the statistical lifetime of excited states to discriminate between respective pluralities of bound and unbound dye molecules, and the difference is exaggerated or amplified by the use of time-gating.

Specifically, where the excited states of two species of particles (e.g. bound and unbound dyes) statistically decay at respectively different rates, a determination is made of fluorescent emission intensity during a predetermined interval following a delay subsequent to the simultaneous onset of emission decay of both species, which delay is on the order of the $1/e$ decay life (or longer) of the species having the shorter emission lifetime. Such determination provides both detection of the presence and a quantitative measure of the species having the longer emission lifetime, sharply discriminated from the effects of the other species. The term "statistical decay" as used herein is intended to mean the exponential fluorescent intensity decay characteristic of a population of particles initially in an excited state, following cessation of their input excitation energy.

The two species of particles can be, as noted, the same dye molecules in bound and unbound states, or even different molecular species of fluorescent materials, provided that the species exhibit different quantum efficiencies.

Where the species are fluorescent stains or dyes which will bind to organic compounds, a huge number are well known to those skilled in the art. For example, as dyes which preferentially stain proteins such as leucocyte cytoplasm or the granules in granulocytes, one can employ a number of sulfonated triazinyl derivatives such as a diamino stilbene having each amino group in each of the phenyl rings of the stilbene molecule. A typical example of such dye is 4,4'-bis (4-(3 sulfoanilino)-6(bis (2-hydroxy-ethyl)-amino)-1,3,5, triazin-2yl) amino stilbene 2,2'-disulfonic acid tetrasodium salt (hereinafter referred to as LN).

The structure of LN is believed to be as follows:

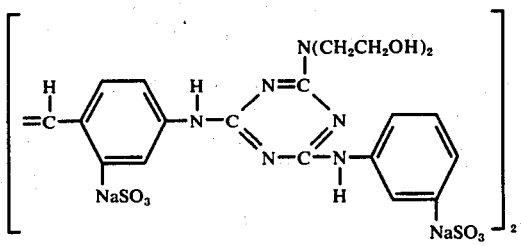

Fluorescent dyes suitable for specifically dyeing eosinophil granules are the anilino or toluidino naphthalene sulfonic acids and their alkyl, alkoxy or halogen substituted derivatives; 4,4' diamino stilbene 2,2' disulfonic acid, N, N, N', N' tetraacetic acid and its alkyl, alkoxy or halogen substitutes derivatives; sulfonated fluorescent derivatives of 1,8 naphthalimide, such as brilliant sulfaflavine and its alkyl, alkoxy or halogen substituted derivatives; 8-p-toluidino-1 naphthalene sulfonic acid and its alkyl, alkoxy or halogen substituted derivatives; and 8-hydroxy-1, 3, 6 pyrene trisulfonic acid and its alkyl, alkoxy and halogen derivatives. These dyes strongly stain the eosinophil granules with a green-blue or green fluorescence.

Dyes which impart a strong fluorescence to nucleic acids preferably are cationic dyes, for example the phenanthridinium dyes such as an ethidium halide, (2,7 diamino - 10 ethyl-9 phenyl phenanthridinium bromide, hereinafter referred to as EB) and its alkyl, alkoxy or halogen derivatives; and in dry smears, acridine orange; and rhoduline orange. The structure of EB is believed to be as follows:

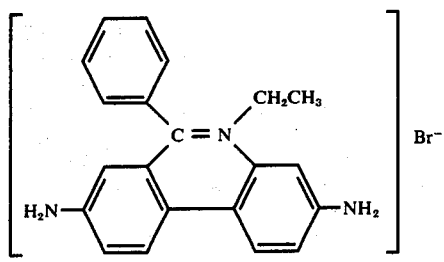

The foregoing listing is not to be considered in any sense exhaustive of the dyes which are suitable for use in the present invention. Indeed, a large number of other fluorescent dyes which can be used are described in *Biological Stains*, R. D. Lillie, the Williams & Wilkens Co., Baltimore, 1969.

Referring now to the systems of the invention shown in FIG. 1, there will be seen, in block schematic form, a sample 20 of minute specimens (not shown) in a liquid medium, such specimens having bound thereto molecules of an appropriate fluorescent dye so as to form a first species of fluorescent particles. A second species is, for example, constituted of the same dye present in free or unbound form in the liquid medium. The present invention comprises light source 22 which can be any of a number of sources of excitation radiation which will stimulate or induce fluorescent emission from the dye molecules of both species in sample 20.

Light source 22 may itself be a narrow band source of light matched to the fluorescence excitation wavelength band of dye, or can be a broad band source of light together with appropriate filtering. The term "light" as used herein is intended to include not only visible radiation but radiation particularly in the ultraviolet region as well. Thus, light source 22 can be any of a number of lasers selected according to the nature of the output wavelength band or typically can be a high intensity, broadband source e.g. a carbon arc or the like, together with appropriate passband filtering such as can be provided by an interference filter. For example, when using LN as the dye, one would employ a light source having high intensities in the wavelength band in the range of 320 to 390 m$\mu$. For anilino and toluidino naphthalene sulfonic acids, light source 22 should be selected to provide a strong output intensity in the range of 320 to 410 m$\mu$. Similarly, the output of light source 20 when using brilliant sulfaflavine as the dye should be in the range of 360 to 450 m$\mu$, and when ethidium bromide is employed as the dye, light source 20 should provide a strong output intensity in the range of 480 to 550 m$\mu$.

Fluorochrome dyes particularly exhibit higher quantum efficiencies when bound to an organic substrate than when unbound. With regard to dyes which have such differential quantum efficiencies depending upon the bound or unbound state, free or unbound molecules in the background liquid will exhibit, when stimulated, a fluorescence which statistically decays much more quickly than the dye molecules which are bound to an organic substrate. To take optimal advantage of the difference in decay rates to discriminate between the sources of the fluorescence, time gating means such as modulator 24 are provided for modulating the intensity of the radiant output from source 22. Preferably, such modulation operates so that light from source 22 directed onto sample 20 irradiates the sample periodically between some minimal or dark level (preferably zero radiation), and a maximum intensity, with very short rise and fall times. The fall time of the exciting radiation from source 22 as modulated by modulator 24 should not be more than the same order of magnitude and preferably shorter than the decay time of the fluorescent emission from the unbound dye molecules. The "decay time", of course, is the time requires for the intensity of fluorescence to decay to a fraction, 1/e of its original intensity.

Thus, modulation of light source 22 can be achieved for example by mode-locking the latter, in the case where light source 20 is a known-type of pulsed laser, for example, a Model 165 laser commercially available from Spectraphysics Co., Mountain View, California. In such case, modulator 24 would be the mode locking control, such as Spectraphysics' piezoelectric Model 361 mode locker driven by a 70 MHz oscillator. Alternatively, light source 22 could be a continuous wave source and modulation of the source can be provided by insertion of an extremely high-speed chopper such as a Pockels effect device between the continuous wave source and sample 20. In this latter instance, modulator 24 would comprise both the Pockels effect device and the pulse field generator which provides the requisite electrical field. In either case, modulator 24 can provide an electrical signal which controls or is synchronous with the modulation of light from source 22.

The modulated light from source 22 is directed onto sample 20 containing a suspension of dyed specimens in liquid. The energy irradiating the molecules of fluorescent material should not be intense enough to cause bleaching. Bleaching can be defined as the tendency of many molecules, when raised to a highly excited state by energy input, to photodecompose or readily react chemically with other materials such as dissolved oxygen or the like, thereby so altering the molecule that it loses its ability to fluoresce.

Light emitted from the irradiated sample is filtered by wavelength filter 26. The passband of the latter is selected so as to discriminate between light from source 22 and stray radiation on the one hand, and characteristic wavelengths of the fluorescence from the molecules of the particular dye used to stain the particles in sample 20. Typically filter 26 is an interference filter or other known type of filter, the passband characteristics of which can be precisely and narrowly tailored around specific central wavelengths. Light transmitted by filter 26 is preferably further transmitted through viewing optics 28 to detector 30. Optics 28 are typically either reflective, refractive or catadioptric systems which serve to collect light and concentrate same to a focal point. Detector 30 can be any of a large number of photoelectric systems, such as known photomultipliers, which provide at an output terminal 32 an electrical output signal having a parameter, such as amplitude, proportional to the intensity of light incident thereon. Typically, one can employ a focussed photomultiplier such as the Model VPM-153a made by Varian Associates, Palo Alto, California which provides a gain of about $10^5$ and exhibits rise and fall times of about 150 picoseconds or less.

As noted, means are provided for determining, following exposure of particles in sample 20, the amplitude of fluorescent emission from bound dye molecules, but only after the intensity of fluorescent emission from unbound dye molecules in the suspending liquid in sample 20 has decayed below a preset level, for example to the fraction $1/e$ of its original intensity. This is accomplished by sampling, either directly or indirectly, the fluorescent emission in delayed synchronism with the modulation of the exciting radiation. In the embodiment of FIG. 1 for example, the output of the detector is examined starting a predetermined time after the light from source 22 has been modulated to its minimum or "off" intensity. Thus, electronic gating or switching means 34, typically a field-effect transistor, diode or other fast known gate, is disposed for coupling and decoupling the output terminal 32 of detector 30 and the input terminal of amplifier 36 in accordance with electrical signals received from phase delay device 38. The latter which may be any of a number of known delay lines or the like, is connected for example to the frequency driver of modulator 24 so as to provide an output electrical signal which phase lags the line frequency of the modulator by a predetermined time or phase delay determined for example, in accordance by the known decay time of the unbound dye. The output of delay device 38 is coupled to gating means 34 for controlling the switching of the latter. Lastly, the output of amplifier 36 is connected to the input of means 40 which is typically a cathode ray oscilliscope, a digital display device or any other of a large number of known systems for displaying or storing electrical signals. In this system then, the detector continuously detects the fluorescence and only a selected portion of the electrical output signal from the detector is sampled. Sampling can be instead made directly of the fluorescence itself by triggering or gating the operation of the detector, i.e. turning the latter on and off at the proper times. Alternatively, instead of sampling either the detector input or output signals, one can sample the amplified signal from amplifier 36 by selective modulation of display 40.

The operation of the system of FIG. 1 can be advantageously described in connection with the idealized waveform in the timing diagram of FIG. 2 wherein there are shown three wave forms, designated A, B and C, all on a common time base or abscissa. The ordinate of each wave form is exemplary of amplitude. In FIG. 2A, there is shown the amplitude of light from source 22 modulated by modulator 24 in an on-off mode to commence at time T, with an abrupt (or ideally instantaneous) rise time and at least an equally abrupt cessation at time $T_2$ thereby providing an idealized rectangular amplitude pulse of width $w$. Preferably, source 22 is modulated by modulator 24 to provide a plurality of like pulses each of width $w$ at a repetition rate having a period R. Where sample 20 is exposed to the modulated pulse of FIG. 2A, the dye molecules in the sample will (the pulse containing wavelengths within the absorption bands of the dye molecules and of intensity sufficient to excite fluorescence) then commence to radiate at their characteristic fluorescent wavelengths. FIG. 2B shows a waveform exemplary of the fluorescence characteristic of unbound dye molecules during the period R, rising to a maximum during the interval $T_1$ to $T_2$, and decaying exponentially and very quickly from the time $T_2$ (when the pulse amplitude in FIG. 2A has become minimal) to the level of $1/e$ at time $T_3$. Preferably, the delay introduced into the signal from modulator 24 by delay device 38 is the time interval between time $T_2$ and $T_3$ so that amplifier 36 observes the signal from detector 30 only beginning at time $T_3$.

The waveform of FIG. 2C is exemplary of the fluorescence emission characteristic of a population of bound dye molecules in sample 20 and typically thus reaches a maximum between times $T_1$ and $T_2$ in the same manner as the unbound dye molecules typified by FIG. 2B. However, it will be seen that in FIG. 2C although the decay of fluorescence from the bound dye molecules is also exponential, the decay time is considerably longer. Hence at time $T_3$, when the unbound dye molecule fluorescence, as exemplified by FIG. 2B, has decayed to a very low or nominal amplitude the amplitude of the fluorescence from the bound molecules is still very high and the ratio of signal (fluorescence from the bound dye) to background or noise (fluorescence from the unbound dye) is considerably better at time $T_2$ than at any time between $T_1$ and $T_3$. Reading of the signal from detector 30 by amplifier 36 preferably continues for some time interval to time $T_4$ prior to the next pulse from source 22 and while the amplitude of the waveform of FIG. 2C has remains approximately as much greater than the waveform of FIG. 2B as at time $T_3$.

It will therefore be seen that the use of time-gating permits one to discriminate very sharply between emissions from two populations of fluorescent dye molecules which exhibit respectively different excited-state lifetimes, such as may be simply due to the difference in binding state. This technique is particularly applicable to molecules which fluoresce, not by direct absorption of exciting radiation, but by energy transfer (such as by tunnelling) from adjacent molecules which serve as absorbers. The emission from such energy transfer fluorescing (ETF) materials tends to reach a peak only after some delay occasioned by the transfer phenomenon. Thus in the case where one of the species of particles is such an ETF material, the delay prior to determination of fluorescent emission is then not necessarily based on the 1/e decay life of the species having the shorter emission time. Instead, one can provide a pulse of stimulating radiation which raises one species to full emission intensity substantially instantaneously by direct absorption, but which is so short that the pulse has been modulated "off" well before the ETF material has reached peak emission. Even if both species have the same decay rate, if one delays determination of emission until peak emission of the ETF material has been reached, it is apparent that the present method can provide a superior technique for discriminating energy transfer type of fluorescence from background and other emissions.

Since certain changes may be made in the above apparatus and method without departing from the scope of the invention herein involved, it is intended that all matter contained in the above description or shown in the accompanying drawing shall be interpreted in an illustrative and not in a limiting sense.

What is claimed is:

1. Method of distinguishing between two species of fluorescent particles in a mixture of said species, which species have respectively different fluorescent quantum efficiencies and corresponding decay lifetimes, but fluoresce at substantially a common wavelength band, said method comprising the steps of
    substantially simultaneously irradiating said particles in said mixture with radiation capable of stimulating fluorescent emission from both said species, but not intense enough to cause bleaching;
    reducing the intensity of said radiation so as to permit fluorescent emission from both of said species to decay statistically; and
    measuring after a delay determined as a function of the shorter of said decay lifetimes following reduction of said radiation intensity, the intensity of said fluorescent emission at said wavelength band during a predetermined time interval.

2. Method as defined in claim 1 wherein said radiation intensity is reduced so as to permit the fluorescent emission from both of said species to statistically decay from substantially the same initial time, and the interval of said delay is determined from said initial time.

3. Method as defined in claim 2 wherein said delay is determined to be not substantially less than the time required for the fluorescence from the one of said species having the shorter decay time to decay to a value of about $1/e$.

4. Method as defined in claim 1 including the step of dyeing organic material with a fluorescent dye so that a first of said species comprises the dye molecules bound to said organic material and the second of said species comprises the dye molecules not bound to said organic material.

5. Method as defined in claim 1 wherein said radiation is substantially monochromatic coherent radiation having wavelengths substantially in absorption bands of said species.

6. Apparatus for discriminating between two fluorescent particulate species having respectively different fluorescent decay lifetimes, in combination,
    a laser for providing radiation capable of stimulating fluorescent emission from said species, and disposed for irradiating said species,
    means for modulating the intensity of radiation from said laser and including a mode locker coupled to said laser, and a source of oscillating signals for driving said mode locker; and
    means for sampling the intensity of fluorescent emission from said species in delayed synchronism with the modulation of said intensity of radiation.

7. Apparatus as defined in claim 6 wherein said means for sampling comprises means responsive to said means for modulating so as to provide a measurement of said emission during a time interval commencing after a predetermined delay following modulation of said intensity of radiation to a selected low level.

8. Apparatus as defined in claim 6 wherein said means for sampling comprises means for producing an electrical output signal responsively to said fluorescent emission and positioned for detecting said emission, and means for gating said output signals from said detector means.

* * * * *